US012533455B2

(12) United States Patent
Moroz

(10) Patent No.: US 12,533,455 B2
(45) Date of Patent: Jan. 27, 2026

(54) SYSTEM AND METHOD OF HAEMODIALYSIS

(71) Applicant: Moroz Technologies Pty Ltd., Gnangara (AU)

(72) Inventor: Paul Moroz, Gnangara (AU)

(73) Assignee: Captere Pty Ltd (AU)

( * ) Notice: Subject to any disclaimer, the term of this patent is extended or adjusted under 35 U.S.C. 154(b) by 439 days.

(21) Appl. No.: 17/922,732

(22) PCT Filed: May 10, 2021

(86) PCT No.: PCT/AU2021/050430
§ 371 (c)(1),
(2) Date: Nov. 1, 2022

(87) PCT Pub. No.: WO2021/222991
PCT Pub. Date: Nov. 11, 2021

(65) Prior Publication Data

US 2023/0166020 A1 Jun. 1, 2023

(30) Foreign Application Priority Data

May 8, 2020 (AU) ................................ 2020901487
Aug. 28, 2020 (AU) ................................ 2020903092
Mar. 12, 2021 (AU) ................................ 2021900724

(51) Int. Cl.
*A61M 1/36* (2006.01)

(52) U.S. Cl.
CPC ........ *A61M 1/3687* (2013.01); *A61M 1/3618* (2014.02); *A61M 1/3681* (2013.01); *A61M 2202/0413* (2013.01)

(58) Field of Classification Search
CPC .............. A61M 1/3687; A61M 1/3618; A61M 1/3681; A61M 2202/0413; A61M 1/14;
(Continued)

(56) References Cited

U.S. PATENT DOCUMENTS 4,865,841 A * 9/1989 Balint, Jr. ........... A61M 1/3486 530/391.1
2005/0215936 A1* 9/2005 Gorsuch ............. A61M 1/1678 604/6.01

(Continued)

FOREIGN PATENT DOCUMENTS

WO 2009155384 A1 12/2009
WO 2016077067 A2 5/2016

OTHER PUBLICATIONS

Xiao, H., & Cezar, N. (2005). Cationic-modified cyclodextrin nanosphere/anionic polymer as flocculation/sorption systems. Journal of colloid and interface science, 283(2), 406-413. (Year: 2005).*

(Continued)

*Primary Examiner* — Adam Marcetich
(74) *Attorney, Agent, or Firm* — Endurance Law Group PLC

(57) ABSTRACT

The present disclosure provides a method of removing a target substance from blood of a patient, the method comprising steps of: providing a complexing agent, especially a supra-molecular compound or core particle, adapted for selectively binding a target molecule or target entity in the blood of the patient in a complex, e.g. a supra-molecular complex; administering the complexing agent into the patient's blood, preferably into an extracorporeal blood flow pathway, for binding with the target molecule or the target entity; conveying the blood having the complexing agent through a treatment zone of an extracorporeal blood flow pathway for a predetermined period of time to bind or incorporate the target molecule or target entity within the blood in a complex, such as a supra-molecular complex; and removing the complex (e.g. supra-molecular complex) from the blood by haemodialysis, which preferably includes one or more of filtration, ultrafiltration, convection, or adsorption. The disclosure thus also provides a system (1) for
(Continued)

removing a target substance from blood of a patient, the system (1) comprising: an extracorporeal blood flow pathway (2) for connection to a patient and for guiding or conveying a flow of blood from the patient along the pathway; a treatment zone (5) arranged in the extracorporeal blood flow pathway (2) for mixing a complexing agent (C) with the blood adapted to bind a target molecule (M) in a complex (X), especially a supra-molecular complex or core particle complex, as the blood flows through the treatment zone (5); and a haemodialysis unit (4) for separating the complex (X) from the blood via one or more of filtration, ultra-filtration, convection, and membrane adsorption, with or without magnetic assistance.

23 Claims, 2 Drawing Sheets

(58) Field of Classification Search
CPC ..... A61M 1/15; A61M 1/3622; A61K 9/5115; A61B 18/18; A61B 2018/00398
See application file for complete search history.

(56) References Cited

U.S. PATENT DOCUMENTS

2005/0274672 A1* 12/2005 Tu ........................ B01D 61/145 210/645
2007/0073264 A1* 3/2007 Stedman ............... A61M 25/10 604/500
2009/0054823 A1* 2/2009 Bridges ............... A61M 1/3659 604/6.09
2009/0156976 A1* 6/2009 Korbling ................. A61P 35/00 977/734
2010/0100027 A1* 4/2010 Schilthuizen ....... A61M 1/1696 210/287
2011/0098623 A1 4/2011 Zhang et al.
2012/0263793 A1* 10/2012 Vitaliano ............. G01N 21/648 424/490
2013/0095039 A1* 4/2013 Lu ...................... A61K 41/0052 424/9.1
2015/0246170 A1 9/2015 Miao et al.
2015/0283318 A1 10/2015 Wang et al.
2017/0049950 A1* 2/2017 Felder ................. A61M 1/3679
2017/0119891 A1* 5/2017 Lal ....................... A61K 9/5192
2018/0021499 A1* 1/2018 Natan ................... C07C 275/02 604/29
2018/0207106 A1 7/2018 Vitaliano et al.
2020/0246179 A1* 8/2020 Peyman ................. A61B 18/20

OTHER PUBLICATIONS

Aumiller Jr., et al. "Protein cage assembly across multiple length scales," Feb. 7, 2018, Chemical Society Reviews, vol. 47, 97 pages.
Heddle, et al. "Natural and artificial protein cages: design, structure and therapeutic applications," Current Opinion in Structural Biology, Mar. 27, 2017, vol. 43, pp. 148-155.
Vu, et al. "Immunoglobulin deposition on biomolecule corona determines complement opsonization efficiency of preclinical and clinical nanoparticles," Nature Nanotechnology, Jul. 14, 2019, vol. 14, 25 pages.
Yigit, et al. "MRI Detection of Thrombin with Aptamer Functionalized Superparamagnetic Iron Oxide Nanoparticles," Bioconjugate Chemistry, 2008, vol. 19, pp. 412-417.

* cited by examiner

SYSTEM AND METHOD OF HAEMODIALYSIS

This application claims priority from Australian provisional patent application no. 2020901487 filed 8 May 2020, Australian provisional patent application no. 2020903092 filed 28 Aug. 2020, and Australian provisional patent application no. 2021900724 filed 12 Mar. 2021, and the contents of each of these applications are incorporated herein by reference in their entirety.

TECHNICAL FIELD

The present disclosure relates to a system and method of haemodialysis for the removal of metabolic waste products and/or other undesirable haematologic entities, such as various molecular structures, toxins, cells and microorganisms, from blood. Thus, the present disclosure also relates a system and method for treating hematologic pathologies that include, but are not limited to, infections, neoplasms, and molecular, renal, hepatic, metabolic and immunologic disorders.

The invention will be described herein in the context of its application in treating patients suffering chronic renal failure (CRF) whose kidneys can no longer perform such functions naturally. It will be understood, however, that other fields of application exist, and, in particular, other types of patients for whom removal of metabolic waste products, excess water, solutes, toxins, molecular structures and/or microorganisms from the blood will also be of critical importance although these patients may not suffer CFR. The invention will also be described herein in the context of its application in treating blood-borne infectious pathogens and associated molecular hematologic abnormalities.

BACKGROUND ART

The following discussion of background is intended to enable an understanding of the present disclosure only. This discussion is not an acknowledgement or admission that any of the material referred to is or was part of the common general knowledge as at the date of this patent application.

CRF causes serious disturbances in water and electrolyte balance in the blood as well as an accumulation of toxic metabolites that cause major morbidity and mortality in CRF patients. When considering haemodialysis, the mainstay of treatment for millions of patients suffering from CRF, whole blood can be considered to comprise three size classes of constituents; namely: (i) small molecules (SM) which are substances typically having a size less than 1.5 nm such as water, electrolytes and other small molecules; (ii) mid-sized molecules (MM) having a mass in the range of about 500 Da to 50 kDa or a size in the approximate range of 1.5 to 3 nm; and (iii) large molecules and structures (LMS) having a size typically over 3 nm and up to many microns in size, including larger proteins, supra-molecular structures and blood cells.

Haemodialysis operates very well to remove excessive amounts of SM (such as electrolytes, inorganic molecules and small proteins of <500 Da) via the mechanisms of diffusion, osmosis, and ultrafiltration. The processes of ultrafiltration and convection in haemodialysis are also usually quite successful in separating LMS from SM and MM in the blood. The processes of convection and membrane adsorption are the mechanisms employed in haemodialysis for removing MM, but these mechanisms are significantly less effective than the respective processes employed for SM and LMS.

Thus, the suboptimal removal of mid-sized molecules, e.g. 500 Da-50 kDa proteins, during haemodialysis remains problematic and is a major cause of increased morbidity and mortality for CRF patients. By way of illustration, the blood concentration of MMs remains in the range of 1.5 to 200 times greater for CRF patients. MM proteins include, for example, beta-2 microglobulin (B2M), tumour necrosis factor alpha (TNFa), TFT-23, transthyretin, many other interleukins and cytokines, immunoglobulin light chains and parathyroid hormone. These compounds are known to play a role in various conditions, including, atherosclerosis, myocardial infarction, amyloidosis, decreased immune function, protein energy wasting, stroke, acute systemic inflammatory response syndrome (SIRS) and chronic inflammatory conditions, such as rheumatoid arthritis and inflammatory bowel disease. Patients with acute and chronic inflammatory conditions (e.g. Crohn's disease and rheumatoid arthritis) or severe infections (e.g. COVID-19, MRSA, Ebola) experience excessive systemic inflammatory response syndrome (SIRS) that can worsen symptoms and directly lead to death. Another approach to treating severe infections involves attempts to reduce the impact of the SIRS which is mediated by cytokines released by immune cells in response to cell damage cause by the infection. By inhibiting the activity of various cytokines, it may be possible to attenuate the SIRS and hence reduce morbidity and mortality from virulent infections. Patients who have suffered trauma in both civilian and military settings may also benefit from a system of rapid blood debridement of various molecular structures, toxins, cellular fragments and microorganisms. Albumen (2.5 nm) is also a MM, but it is preferable not to remove this molecule from blood plasma due to its importance in maintaining plasma oncotic pressure.

In view of the above, it would be desirable to provide a new system and method for improved removal of MM from the blood. Greater success in this area would lead to improved outcomes for patients suffering CRF, serious infections, and/or various acute and chronic inflammatory conditions. It would also be desirable to provide a new system and method of treating hematologic pathologies.

SUMMARY OF THE DISCLOSURE

According to one aspect, the disclosure provides a method of haemodialysis for removing waste products and/or undesirable substances from the blood of a patient, the method comprising steps of:

- providing a complexing agent, especially a supra-molecular compound or a core particle, adapted for selectively binding or incorporating a target molecule, a molecular structure, or a pathogen to be targeted in a patient in a complex, like a supra-molecular complex;
- administering the complexing agent into the patient's blood, preferably into an extracorporeal blood flow pathway, for binding with the molecule, molecular structure, or pathogen to be targeted;
- conveying blood containing the complexing agent through a treatment zone of an extracorporeal blood flow pathway for a predetermined period of time for binding the target molecule, molecular structure, or pathogen in a complex, e.g. a supra-molecular complex; and
- after the predetermined period of time, removing the complex (supra-molecular complex) from the blood via a haemodialysis, preferably via one or more of filtration, ultrafiltration, convection, or adsorption.

The disclosure thus provides a complexing agent-mediated haemodialysis or blood filtration technique that augments established blood filtration systems to bind and then filter specific pathogens or molecules from the blood. In particular, the disclosure is designed to target mid-sized molecules (MM) having a mass in the range of about 500 Da to 50 kDa and/or a size in the approximate range of 1.5 to 3 nm, which have hitherto presented difficulties in achieving effective removal.

In a preferred embodiment, the complexing agent adapted to selectively bind or incorporate a target molecule, target molecular structure, or target pathogen in a supra-molecular complex may be provided in the form of a supra-molecular compound.

Supra-molecular chemistry is a field of chemistry concerning chemical systems composed of a discrete number of molecules. The strength of the forces responsible for spatial organization of the system range from weak intermolecular forces, electrostatic charge, or hydrogen bonding to strong covalent bonding, provided that the electronic coupling strength remains small relative to the energy parameters of the component. "Host-guest" chemistry is a branch of supra-molecular chemistry in which a "host" molecule or compound forms a chemical complex with a "guest" molecule or ion. Host-guest chemistry relates to complexes that are composed of two or more molecules or ions that are held together in unique structural relationships by forces other than those of full covalent bonds. Host-guest chemistry encompasses the idea of molecular recognition and interactions through non-covalent bonding. Non-covalent bonding is critical in maintaining the 3D structure of large molecules, such as proteins and is involved in many biological processes in which large molecules bind specifically but transiently to one another. The two components of the complex are held together by non-covalent forces, most commonly by hydrogen-bonding. Binding between host and guest is usually highly specific to the two moieties concerned. The formation of these complexes is central to the subject of molecular recognition. The "host" component can be considered the larger molecule or compound, and typically encompasses the smaller "guest" molecule. In biological systems, the analogous terms of "host" and "guest" are commonly referred to as enzyme and substrate, respectively.

In the context of the present disclosure, therefore, it will be appreciated that the term "supra-molecular compound" as used herein (i.e., throughout the description and claims of this specification) may be understood as a supra-molecular host molecule, structure, or compound for binding with the target molecule as a "guest" molecule.

In a preferred embodiment, the supra-molecular compound is an encapsulating supra-molecular structure in the form of a molecular cage, such as an ultra-large cage structure (ULCS) protein. A ULCS protein can be designed to have an opening of a size and binding affinity for specific mid-sized molecule. Under correct conditions, therefore, it may be possible for a ULCS to selectively bind a mid-sized molecule (MM) for which it has been designed. In this way, the MM is encapsulated within a ULCS protein to form a supramolecular mid-sized molecule complex (SMMC). The SMMC is much larger than the MM alone. The increased size of the selected MM thus allows for it to be separated from small molecules. As the SMMC will typically be a smaller-sized component among the larger molecules, its enhanced removal by ultrafiltration or convection is envisaged. The encapsulation of the MM by a correctly designed ULCS can also facilitate removal of the MM by membrane adsorption within the dialysis fibrils. If the ULCS has outward facing moieties that have increased affinity for moieties on the adsorption membrane, then this pathway of MM removal can also be enhanced. Thus, the external moieties on complexing agent may bind to complimentary moieties on an adsorption membrane in the haemodialysis process. In addition to or in place of specific moieties on the ULCS, a ferromagnetic nanoparticle could be incorporated into the ULCS to enable the SMMC to be extracted by the application of a magnetic field during the haemodialysis process; e.g. magnetic filtration or magnetic microfiltration.

In a preferred embodiment, instead of using an encapsulating cage structure, the supra-molecular compound may include a number of individual molecules adapted to bind to the MM and to each other in a form of polymerization of the MM or flocculation of MM into larger aggregates. Electromagnetic radiation (EMR) can promote flocculation and agglomeration of proteins or supra-molecular structures (SS). In particular, EMR can alter the structure and function of proteins and/or the lattice conformation of various supra-molecular structures. For example, pulsed electric or magnetic fields, microwaves, radiofrequency waves and gamma rays have been evaluated in this field. It is therefore envisaged to flocculate MM bound to SS on exposure to appropriately selected EMR.

In a preferred embodiment, the supra-molecular compound belongs to a class of molecules that includes any one or more of: ultra large cage structures, coordination cages, calixerenes, clathrates, crown ethers, keplerates, metalloprisms, and geometric arrangement of fullerenes capable of capturing a target structure. The supra-molecular compound may optionally contain one or more magnetic nanoparticle (s) incorporated or embedded therein to facilitate use of magnetic filtration in the dialysis. Alternatively, the supra-molecular compound may have outward facing moieties matched for optimal binding to an adsorption membrane during the subsequent dialysis.

In another embodiment, the complexing agent adapted for selectively binding or incorporating the target molecule or molecular structure in a supra-molecular complex is provided in the form of a core particle. To this end, the core particle may be coated with one or more receptors or binding sites for selectively engaging with the hematogenous target molecules and structures for their subsequent removal during dialysis.

In a preferred embodiment, the core particle complexing agent may comprise a magnetic or non-magnetic particle ranging from approximately 100 nm to 1 micron. The particle may be coated with receptors, zeolites or supra-molecular structures to form the binding sites for selectively engaging with the target molecule or molecular structure. In this regard, the core particle complexing agent may comprise a superparamagnetic iron oxide nanoparticle (SPION) typically of a size/diameter in the range of about 1-150 nm, a cluster of SPIONs, or a magnetic microbead (MMB) typically of about 1 micron or less (e.g. $Fe_2O_3$). Non-magnetic particles, preferably in the same size range, may comprise simple benign organic polymers. In both cases, the core particles act as anchors or cores for receptors or binding sites, such as zeolites or supramolecular structures, that can bind the target molecules or target entities. The magnetic particles offer the added option of magnetic filtration in the dialysis process.

Receptor molecules and supramolecular compounds such as ULCS, including unconventional cages formed by fullerenes, can be attached to an outer surface of both magnetic and non-magnetic core particles as complexing agents. These receptors and supramolecular compounds can be specific for middle molecules, cytokines, interleukins and, in the case of receptors, for microorganisms such as such as COVID-19, MRSA, Ebola and VRE. All of these middle molecules and pathogens will bind to well-known specific receptor molecules on cells and various tissue. Particles coated with these receptors or supramolecular compounds capable of host-guest interactions will thus be able to bind target entities to upsize them and so facilitate their subsequent removal by dialysis with or without magnetic augmentation. An example is a SPION or MMB for binding tumour necrosis factor alpha (TNFA, approximately 1.6 nm), which is a potent driver of SIRS. Infliximab (approximately 3.5 nm) is a monoclonal antibody that binds to and inhibits one or two TNFAs. A single SPION or MMB coated with infliximab could potentially bind several or possibly even hundreds of TNFAs that could subsequently be removed by filtration.

Zeolites are naturally occurring or synthetic alumina-silicates (e.g. $AlO_4^{5-}$, $SiO_4^{4-}$) that form three dimensional tetrahedral arrays containing holes or channels in their lattice structure that enable them to exchange ions and to act as molecular sieves. They can be constructed to bind/capture proteins. Magnetic and non-magnetic core particles coated with such zeolites may thus trap middle-sized molecules and other target entities with subsequent dialysis extraction. Zeolites may have an advantage over specific core particle receptors and supra-molecular compounds of being able to bind a range of target middle-sized molecules depending upon the size of their interstices. In a similar way, supra-molecular structures comprised of fullerenes ($C_{60}$) may have a corresponding advantage.

In this disclosure, the terms "supra-molecular compound" or "supra-molecular structure" are used to refer to a discrete molecule, such as an ultra large cage structure (ULCS) molecule, calixerene, crown ether, clathrate, fullerene arrangement or other molecule that would fall within the realm of supra-molecular chemistry outlined above. The term "core particle" is used to refer to a magnetic or non-magnetic particle in the range of about 1 nm to 1 micron to which is attached one or more specific receptors or binding sites, such as supra-molecular compounds or zeolites. In the context of the disclosure, therefore, the term "complexing agent" will be understood to encompass both "supra-molecular compounds" and "core particles" adapted for binding with a target molecule or target molecular structure or pathogen, and both will be understood to form a "supra-molecular complex" with the target entity. It will be appreciated, however, that a complex formed with "core particles" may also be referred to herein as a "core-particle molecular complex".

In a preferred embodiment, the method comprises administering or infusing the complexing agent into extracorporeal blood as the blood exits a patient's body along the extracorporeal pathway. In an alternative embodiment, the step of administering the complexing agent comprises introducing or infusing the complexing agent into the patient's bloodstream at some time (e.g. one or more hours) prior to performing haemo-dialysis to provide time for the supra-molecular complex to form in vivo.

In a preferred embodiment, the method comprises conveying the blood through the treatment zone for a predetermined period of time, preferably in the range of several minutes; e.g. in a range of about 2 to 20 minutes. The conduit carrying the blood in the treatment zone preferably contains a volume of at least about 100 ml, more preferably in the range of about 200 ml to 300 mL of whole blood, for at least several minutes to allow time for the complexing agent, e.g. the supramolecular compound or core particle, to complex with the mid-sized molecule or target entity.

In a preferred embodiment, the method comprises altering physical or chemical conditions of the blood in the treatment zone to promote complexing of the mid-sized molecule with the complexing agent. For example, the method may comprise altering any one or more of the pH, temperature, and composition of the blood in the treatment zone to promote formation of the complex. The method may also include agitating the treatment zone and/or applying some form of electromagnetic radiation (EMR) to the treatment zone to promote formation of the complex and/or to cause an aggregation or flocculation of multiple complexes into clusters.

In a preferred embodiment, the method comprises separating or dividing the blood flow along the extracorporeal blood flow pathway into two streams, a first stream comprising substantially small molecules (SM) typically having a size less than 1.5 nm, including water and electrolytes, and a second stream comprising larger molecules (LM) typically having a size of over 3 nm and up to many microns, including larger proteins, supra-molecular structures or core particles and blood cells. In this way, the two steams may then be processed separately in the dialysis unit. The first stream will desirably include albumen, which at a size of about 2.5 nm qualifies as a mid-sized molecule. But it is preferable not to remove albumen from the plasma due to its importance in maintaining plasma oncotic pressure.

In a preferred embodiment, therefore, the method comprises processing the first and second streams of the extracorporeal blood flow pathway separately in a haemo-dialysis unit. The supra-molecular complexes created by the complexing agent binding with the mid-sized molecules are carried in the second stream. As these complexes are larger and have different physio-chemical properties to normal mid-sized molecules, they can be better removed via ultrafiltration, convection, or adsorption, with or without magnetic assistance. The first stream carrying the small molecules is dialysed in the usual way.

In a preferred embodiment, the method comprises recombining the first stream and second stream into a unified extracorporeal blood flow prior to returning the blood to the patient.

According to another aspect, the disclosure provides a haemodialysis system for removal of metabolic waste products and/or undesirable compounds from the blood of a patient. The system comprises:

an extracorporeal blood flow pathway for connection to a patient and for guiding or conveying a flow of blood from the patient along the pathway;

a treatment zone arranged in the extracorporeal blood flow pathway for mixing of a complexing agent, especially a supra-molecular compound or a core particle, with blood in the extracorporeal blood flow pathway for selectively binding a target molecule, molecular structure, or target pathogen in a supra-molecular complex as the blood flows through the treatment zone; and a haemodialysis unit for separating the supra-molecular complex from the blood via one or more of filtration, ultrafiltration, convection, and membrane adsorption.

Thus, the system is designed to selectively remove undesired molecules sized about 1.5 nm to 3 nm (i.e., not including albumen) from blood by complexing them with one or more agents, such as supra-molecular compounds or core particles, adapted to form a supra-molecular mid-sized molecule complex (SMMC) or a core particle mid-sized molecule complex (CPMC). Such a complex, being significantly larger (over 3 nm) than and having different surface physio-chemical characteristics to the non-complexed MM, is then more amenable to removal from the blood by haemodialysis. This treatment effectively 'upsizes' the MM (except albumen) into a larger structure category, preferably over 100 kDa, e.g. as ultra-large supramolecules (ULSM), enabling removal of the MM category and leaving only the SM (plus albumen) and LMS categories.

In a preferred embodiment, the extracorporeal blood flow pathway is part of a blood flow circuit, especially of a haemodialysis circuit, which is configured to return the blood to the patient. In this regard, the treatment zone is preferably arranged in the extracorporeal blood flow pathway upstream of the blood dialysis unit. Thus, the system is incorporated in or modifies a modern haemodialysis unit so that there is sufficient transit time of whole blood in the treatment zone prior to filtration. During this time, the complexing agent is introduced and any by-products of the treatment can be filtered out of the blood shortly thereafter. Modern haemodialysis equipment can safely circulate at least 100 mL of whole blood extracorporeally through filtration apparatus and return it to the body in several minutes.

In a preferred embodiment, the extracorporeal blood flow pathway for guiding or conveying the blood through the treatment zone is configured such that the blood may remain in the treatment zone for a predetermined period of time of up to several minutes as it flows along the pathway. This provides time for the complexing agent to bind with the mid-sized molecules to form supra-molecular or core particle MM complexes. To this end, the extracorporeal blood flow pathway for guiding or conveying the flow of blood in the treatment zone may be one or more of extensive, convoluted, serpentine and tortuous. This provides for an extended duration or time for the blood to traverse the treatment zone. The extracorporeal blood flow pathway for guiding or conveying the flow of blood typically comprises tubing; e.g. one or more tubes or catheters.

In a preferred embodiment, the method comprises conveying the blood through the treatment zone for a predetermined period of time, preferably in the range of several minutes; e.g. in the range of 2 to 20 minutes.

In a preferred embodiment, the method further comprises a step of introducing one or more adjuvant compound(s) into the blood before the blood enters the treatment zone for promoting a particular photochemical, electrochemical, or magneto-chemical process in the treatment zone. In this regard, the photo-chemical, electrochemical, or magneto-chemical process may operate to inactivate and/or neutralise microorganisms, pathogens or molecular structures and preferably facilitate their removal from the blood. The adjuvant compound(s), which may be provided as particles, may be introduced into the blood by administering the compound(s) to the patient; e.g. intravenously or orally. Alternatively, the adjuvant compound(s) may be introduced into the blood as it flows along the extracorporeal blood flow pathway. Upon the blood exiting the treatment zone, any such adjuvant process will preferably cease.

In a preferred embodiment, the method is applied in a continuous or on-going series of treatments. For example, in the context of a haemodialysis circuit, in which about 200 ml-300 ml of whole blood is processed extracorporeally by filtration apparatus and returned to the body in several minutes, a series of about 20 to 30 such treatments will typically be necessary to treat an entire adult blood volume. A further series of 20 to 30 such treatments may then be needed as the returned blood in the early treatments will mix with infected blood of the patient that has not yet been treated.

In a preferred embodiment, such a supra-molecular complex filtration system can be used to augment current filtration systems by enabling enhanced targeting of a specific troublesome molecule or substance. This system could be used analogously in renal dialysis and in hepatic failure, where toxic compounds such as mercaptopurines and ammonia may be more completely removed.

In a preferred embodiment, an extra filtration step may be performed prior to a normal dialysis procedure within the haemodialysis unit in which entities in the blood less than 100 kDa are filtered off from the 'upsized' mid-sized molecules and the cellular components. Subsequently a more complete filtration of upsized mid-sized molecules from the much larger cellular components may occur before reconstitution of the cellular components with the other filtered plasma stream.

According to another aspect, this disclosure provides a method of treating hematologic pathologies, such as infections, pathogens, or molecular, metabolic and immunologic disorders, the method comprising steps of:

- providing superparamagnetic nanoparticles, such as superparamagnetic iron oxide nanoparticles (SPIONs), each of which nanoparticles is coated with one or more receptors for binding a molecule or a pathogen, especially a blood-borne molecule or pathogen, to be targeted in a patient;
- administering the coated nanoparticles to a patient, preferably intravenously, so that the coated nanoparticles are available for binding with the molecule or pathogen to be targeted in the patient; and
- after a predetermined period of time, removing the coated nanoparticles bound with the molecule or pathogen from the patient via magnetic filtration, preferably with a magnetic filtration device and/or in conjunction with a haemodialysis unit.

Thus, the present disclosure provides a nanoparticle-mediated, magnetic blood filtration system that may augment established blood filtration systems to bind and then filter specific pathogens or molecules from the blood. More particularly, this aspect relates to the use of superparamagnetic iron oxide nanoparticles (SPION) in a SPION-mediated magnetic blood filtration method. The SPIONs are synthesized coated with receptors for specific molecules that require removal.

In a preferred embodiment, the method further comprises: externally applying a magnetic field locally to the patient to concentrate or accumulate the nanoparticles administered to the patient in a specific area of infection in the patient, such as the lungs or liver, for increased binding with the molecule or pathogen targeted in that area. Thus, the SPIONs are infused systemically into the patient and may be focused over an epicentre of infection in the patient via an externally applied magnetic field; e.g. using an electromagnet. After the receptors coated on the SPIONs become loaded with the target molecule, the SPIONs can then be extracted from the blood using a magnetic filter, preferably in conjunction with a haemodialysis unit.

Thus, this aspect of the disclosure may employ SPIONs coated with receptors for specific molecules or cytokines that mediate SIRS. After systemic infusion, the SPIONs could be temporarily concentrated within a region of the body, such as lungs or liver, by a strong external magnet field applied to the patient, allowing time for increased binding or "mopping up" of cytokines to occur. The SPIONS, loaded with a specific molecule intended for removal, are filtered out of the bloodstream with a magnetic filter integrated in a haemodialysis machine.

In a preferred embodiment, SPIONs with a size in the range of about 50-100 nm could be synthesized coated with receptors specific for certain cytokines, molecules or supramolecular structures. An example is a SPION for binding tumour necrosis factor alpha (TNFA, approximately 1.6 nm), which is a potent driver of the SIRS. Infliximab (approximately 3.5 nm) is a monoclonal antibody that binds to and inhibits one or two TNFAs. As such, a single SPION coated with infliximab could potentially bind dozens (e.g. >100) TNFAs. An external electromagnet placed over the lung fields in an infected patient could concentrate and hold systemically infused SPIONs within the lung fields allowing for greater saturation of SPIONs with TNFA. On relaxation of the magnetic field the SPIONS loaded with TNFA would then pass into the systemic circulation. Ultimately the SPIONS containing bound TNFA (or other molecules) could then be filtered out of the blood as it passes through a haemodialysis/filtration system including a magnetic element. This method could be applied to many other molecular structures and possibly also to microorganisms if a SPION can be effectively coated with the correct receptor molecules.

In a preferred embodiment, the SPIONs may be coated with synthetic zeolites, being microporous aluminosilicates having excellent absorptive and catalytic abilities. These molecular structures could be synthesized to contain pores of appropriate size to capture molecules and possibly microorganisms.

In a preferred embodiment, such a SPION/magnetic filtration system can be used to augment current filtration systems by enabling enhanced targeting of a specific troublesome structure. The system could be used analogously in renal dialysis and in hepatic failure, where toxic compounds such as mercaptopurines and ammonia may be more completely removed. In addition, in a zeolite containing system with pores of only a few nanometres, ions and smaller molecules could be selectively removed.

According to another aspect, the present disclosure provides a batch of super-paramagnetic nanoparticles, such as superparamagnetic iron oxide nanoparticles (SPIONs), wherein each of the nanoparticles is coated with one or more receptors for binding a target molecule or pathogen, especially a blood-borne molecule or pathogen targeted in a patient. Preferably, each of the nanoparticles is coated with a plurality of receptors adapted for binding the molecule or pathogen to be targeted in the patient.

In a preferred embodiment, the nanoparticles are provided in a liquid carrier for administration of the nanoparticles to a patient intravenously. Each of the nanoparticles preferably has a size in the range of about 50-100 nm, and each of the nanoparticles is preferably synthesized coated with one or more receptors for binding certain cytokines, molecules or supramolecular structures, such as tumour necrosis factor alpha (TNFA). For example, each of the nanoparticles may be coated with Infliximab as the receptor for binding with the molecule or pathogen to be targeted.

According to yet a further aspect, the present disclosure provides a system for treating hematologic pathologies, such as infections, pathogens, and/or molecular, metabolic and immunologic disorders. The system comprises: an extracorporeal blood flow pathway for connection to a patient for guiding or conveying a flow of blood from the patient along the pathway; and a treatment zone arranged in the extracorporeal blood flow pathway, the treatment zone including at least one applicator device for applying electro-magnetic radiation (EMR) to blood flowing through the treatment zone along the extracorporeal blood flow pathway. The electro-magnetic radiation (EMR) is applied in a dose or amount to inactivate or to neutralise microorganisms, pathogens, and/or molecular structures in the blood flowing through the treatment zone.

In this way, the system provides for the application of electromagnetic radiation (EMR) to diseased blood external to the patient to result, either directly or indirectly, in the preferential inactivation or neutralisation of pathogens.

In a preferred embodiment, the extracorporeal blood flow pathway is part of a blood flow circuit, especially a haemodialysis circuit, which is configured to return the blood to the patient. In this regard, the treatment zone is preferably arranged in the extracorporeal blood flow pathway upstream of the blood dialysis unit. Thus, the system is incorporated in or modifies a modern haemodialysis unit so that there is sufficient transit time of whole blood in the treatment zone prior to filtration. During this time, the EMR is applied and any by-products of the treatment can be filtered out of the blood shortly thereafter. Modern haemodialysis equipment can safely circulate at least 100 mL of whole blood extracorporeally through filtration apparatus and return it to the body in several minutes.

In a preferred embodiment, the extracorporeal blood flow pathway for guiding or conveying the blood through the treatment zone is configured such that the blood may remain in the treatment zone for a predetermined period of time of up to several minutes as it flows along the pathway. To this end, the extracorporeal blood flow pathway for guiding or conveying the flow of blood in the treatment zone is any one or more of extensive, convoluted, serpentine and tortuous. This provides for an extended duration or time for the blood to traverse the treatment zone. The extracorporeal blood flow pathway for guiding or conveying the flow of blood typically comprises tubing; e.g. one or more tubes or catheters.

In a preferred embodiment, the at least one applicator device for applying the electromagnetic radiation to the blood flowing through the treatment zone along the extracorporeal blood flow pathway is adapted to emit or generate and apply one of: DC (i.e. direct current) electric current, AC (i.e. alternating current) magnetic field, terahertz radiation, visible light, ultraviolet (UV) radiation, X-ray radiation or gamma radiation. In a particularly preferred embodiment, the system includes a plurality of applicator devices in the treatment zone, and the applicator devices may be configured and controlled for applying electromagnetic radiation (EMR) to blood flowing through the treatment zone simultaneously. Such EMRs preferentially inactivate microorganisms by damaging their genetic material or vital protein structures. The application of higher energy EMRs is well established in the treatment of blood components to inactivate lymphocytes and viruses, such as the Epstein-Barr virus (EBV), and it seems safe to apply them to red blood cells and platelets. Furthermore, UV-A radiation has been used with psoralens to photochemically sterilize blood products containing viruses and bacteria.

In this regard, as noted above, a DC electric current (DCEC) of 50-100 micro-amperes applied for a time of three minutes has been demonstrated to inactivate up to 95% of a specimen of HIV 1; a virus with very similar physical characteristics to SARS-CoV-2. Further, pulsed oscillating magnetic fields (OMFs) of five or more Tesla are used to directly kill microorganisms, including viruses, in the food industry. It is possible to safely apply fields of up to 7 Tesla to humans. In addition, ultraviolet radiation (UVR) is used to sterilise surfaces and equipment. As such, these modalities can be applied to extracorporeal human blood to facilitate beneficial electrochemical, magneto-chemical and/or photo-chemical processes in blood for microorganism inactivation or to quench and extract molecules. For example, it is envisaged to apply magnetic fields to alter the spin state of administered reactants in the blood to result in the formation compounds that inactivate microorganisms or cytokines. Another application of magnetic fields could be to provoke polymerization (e.g. dimerization or trimerization) of molecules such as cytokines to inactivate them and cause the formation of large supramolecular structures more amenable to filtration. Similarly, the application of electric fields could potentially catalyse such processes. One form of phototherapy employs visible light in the blue region (wavelength 460-490 nm) to convert insoluble isomers of bilirubin into soluble forms in the treatment of neonatal jaundice—an example of EMR altering the chemistry of a supramolecular structure in the blood. It is envisaged that, under correct conditions, viral killing or inactivating agents may be activated utilising principles of photochemistry.

In a preferred embodiment, the treatment zone is configured to separate the blood into layers, specifically a 'pathogen-rich' layer (i.e. higher pathogen concentration) and a layer of lower pathogen concentration, to provide more targeted application of the EMR from the applicator device(s). This could be facilitated by employing some form of magneto-phoresis or magnetic field flow fractionation as blood leaves the patient and progresses towards dialysis filtration. For example, the treatment zone may include a magnet, such as a DC magnet, arranged to apply a substantially constant magnetic field over an area of the treatment zone for attracting haemoglobin towards that area by virtue of the iron ($Fe^{++}$) ions, thereby displacing pathogens in the blood to an opposite or adjacent region of the treatment zone. A magnetic field could create a roughly vertical (though non-homogenous) gradient through the blood, e.g. comprising microorganisms/pathogens/abnormal molecules located superficially, then other cells and plasma in a middle layer, followed by predominantly red blood cells (RBCs) in a lowermost layer in the vicinity of the magnet. If the therapeutic EMR were applied so as to encounter the superficial layers (containing higher concentrations of pathogens) of this gradient first, the selectivity of treatments could be enhanced, especially in shorter wavelength and higher frequency EMR options. For example, a high frequency terahertz wave (30 Thz) with a wavelength of 10 micron would penetrate a plastic tube containing blood with most of the wave's energy being deposited in the first few millimetres of such a vertical gradient to directly inactivate a microorganism or possibly degrade a molecule; and/or possible terahertz heating of superficial water/plasma containing the microorganisms could be germicidal.

In a preferred embodiment, the plurality of applicator devices may be adapted to emit or generate and apply different types of EMR. In this way, a combination of EMRs could be applied to diseased blood in the treatment zone simultaneously to achieve synergistic effects. Thus, different combinations of EMR, each combination with specific characteristics (e.g. of frequency, wavelength, amplitude) may be tailored to different blood pathologies. Alternatively, a plurality of the applicator devices may be adapted to emit or generate and apply the same type of EMR.

According to another aspect, the disclosure includes a method of treating hema-tologic pathologies, like infections, pathogens, or molecular, metabolic and immunologic disorders, the method comprising steps of: conveying a flow of blood from a patient along an extracorporeal blood flow pathway; and applying electromagnetic radiation (EMR) to the blood flowing in the extracorporeal blood flow pathway in a treatment zone of the blood flow pathway. The electromagnetic radiation (EMR) is applied in a dose or amount to inactivate or to neutralise microorganisms, pathogens, and/or molecular structures in the blood flowing through the treatment zone.

In a preferred embodiment, the step of conveying a flow of blood from a patient along the extracorporeal blood flow pathway involves conveying blood through a blood flow circuit, especially a haemodialysis circuit, which is configured to return the blood to the patient. In this regard, the treatment zone is desirably arranged in the extracorporeal blood flow pathway upstream of a haemodialysis unit.

In a preferred embodiment, the method comprises conveying the blood through the treatment zone for a predetermined period of time, preferably in the range of several minutes; e.g. in the range of 2 to 10 minutes.

As noted above, in a preferred embodiment, a step of applying electromagnetic radiation (EMR) to blood flowing in the extracorporeal blood flow pathway in a treatment zone includes applying one of: DC electric current, AC magnetic field, visible light, terahertz radiation, ultraviolet radiation, X-ray radiation or gamma radiation.

In a preferred embodiment, the method may include applying a substantially constant magnetic field over an area of the treatment zone for attracting haemoglobin towards that area, thereby displacing pathogens in the blood to an opposite or adjacent region of the treatment zone at which the EMR is then applied. In this way, the EMR can better target a pathogen-rich fraction or portion of the blood.

In a preferred embodiment, the method further comprises a step of introducing one or more adjuvant compound(s) into the blood before the blood enters the treatment zone for promoting a particular photochemical, electrochemical, or magneto-chemical process upon application of the EMR in the treatment zone. In this regard, the photo-chemical, electrochemical, or magneto-chemical process operates to inactivate and/or neutralise microorganisms, pathogens or molecular structures and preferably facilitate their removal from the blood. To this end, the adjuvant compound(s) may be introduced into the blood by administering the compound(s) to the patient; e.g. intravenously or orally. Alternatively, the adjuvant compound(s) may be introduced into the blood as it flows along the extracorporeal blood flow pathway. Upon the blood exiting the treatment zone, any such adjuvant process will preferably cease.

BRIEF DESCRIPTION OF THE DRAWINGS

For a more complete understanding of the disclosure and advantages thereof, exemplary embodiments of the disclosure are explained in more detail in the following description with reference to the accompanying drawing figures, in which like reference signs designate like parts and in which.

The accompanying drawings are included to provide a further understanding of the present disclosure and are incorporated in and constitute a part of this specification. The drawings illustrate particular embodiments of the disclosure and together with the description serve to explain the principles of this disclosure. Other embodiments of the disclosure and many of the attendant advantages will be readily appreciated as they become better understood with reference to the following detailed description.

It will be appreciated that common and/or well understood elements that may be useful or necessary in a commercially feasible embodiment are not necessarily depicted in order to facilitate a more abstracted view of the embodiments. The elements of the drawings are not necessarily illustrated to scale relative to each other. It will also be understood that certain actions and/or steps in an embodiment of a method may be described or depicted in a particular order of occurrences while those skilled in the art will understand that such specificity with respect to sequence is not actually required.

DETAILED DESCRIPTION OF THE EMBODIMENTS

Figure 1:
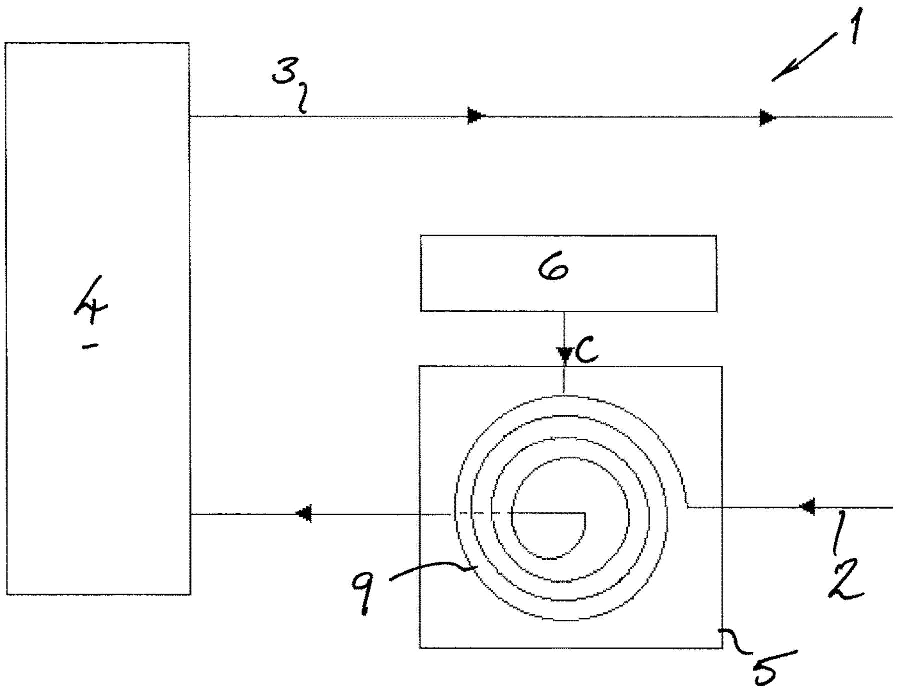
FIG. 1 is a schematic view of a system for treating hematologic pathologies including haemodialysis according to a preferred embodiment.

With reference firstly to FIG. 1 of the drawings, a schematic representation of a haemodialysis system 1 for the removal of metabolic waste products and/or undesirable compounds from the blood of a patient, especially for treating patients suffering chronic renal failure (CRF). The system 1 comprises an extracorporeal blood flow pathway 2 for connection to a patient (not shown) via vascular access obtained in the usual way for conveying a flow of blood from the patient along the pathway 2. In this regard, the extracorporeal blood flow pathway 2 is part of a haemodialysis circuit 3 incorporating a haemodialysis unit 4 and is configured to return the blood to the patient. The system 1 further includes a treatment zone 5 arranged in the extracorporeal blood flow pathway 2 upstream of the dialysis unit 4, with the treatment zone 5 having an infusion device 6 for introducing a complexing agent, such as a supramolecular compound C into the blood flowing through the treatment zone 5 along the extracorporeal blood flow pathway 2. The supramolecular compound C is adapted to bind selectively with a target molecule M in the blood to form a supramolecular complex X which is then to be removed from the blood in the haemodialysis unit 4.

Figure 5:
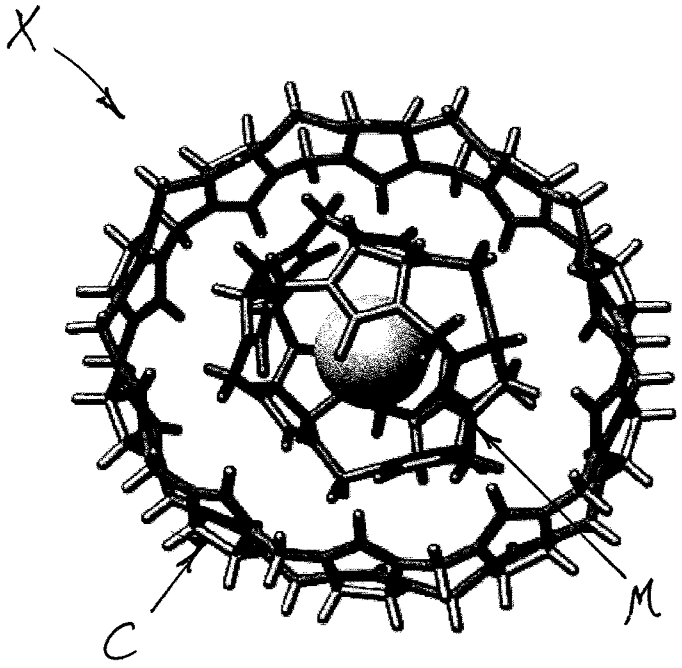
FIG. 5 is a schematic illustration of a supramolecular MM complex in a haemodialysis system and method according to a preferred embodiment.

With reference briefly to drawing FIG. 5, the supramolecular compound C may be supra-molecular structure in the form of a molecular cage, e.g. an ultra-large cage structure (ULCS) protein. The supra-molecular compound C may thus have an opening of a size and binding affinity for the specific target molecule M. Under correct conditions, therefore, it is possible for the ULCS to selectively bind the target molecule M for which it has been designed. In an alternative embodiment, the complexing agent may include a number of individual molecules adapted to bind to the target molecule M and to each other in a kind of polymerization or flocculation of the target molecule M into a complex of clusters or larger aggregates. In another embodiment, the complexing agent may also comprise a core particle in the form of a superparamagnetic iron oxide nanoparticle (SPION), a magnetic microbead (MMB) or non-magnetic organic particle. Such anchor or core particles (e.g. SPIONs of 20-150 nm) can be synthesized coated with receptors or binding sites, such as zeolites, adapted for specific target molecules M that require removal and a number of target molecules M could then bind to each particle to form a complex. Regardless of which form the complexing agent takes (in this case, a supra-molecular compound C) it acts to bind or to incorporate the target molecules M in a complex X (e.g. a supra-molecular complex X) thereby to enlarge or 'upsize' the target molecule M for removal in the haemodialysis unit 4.

The extracorporeal blood flow pathway 2 for guiding or conveying the flow of blood along the haemodialysis circuit 3 comprises tubing 9; e.g. in the form of one or more tubes or catheters. In the treatment zone 5, the tubing 9 of the extracorporeal blood flow pathway 2 defines an extensive and convoluted generally flat spiral pathway such that the blood remains within the treatment zone 5 for a prolonged period of time, preferably in the range of about 2 to 10 minutes, as it flows along the pathway 2. This extended duration for the blood to traverse the treatment zone 5 provides time for the complexing agent (i.e., supra-molecular compound C) to mix with the blood and to bind the target molecule M in the supra-molecular complex X. To facilitate this process, the system and method may involve altering physical or chemical conditions of the blood in the treatment zone 5 to promote complexing of the target molecule M with the agent or supramolecular compound C. For example, the temperature of the blood in the treatment zone 5 may be raised or lowered to promote formation of the supramolecular complex X. Further, the treatment zone 5 may be agitated (e.g. vibrated) and/or some form of electromagnetic radiation (EMR) may be applied to the treatment zone 5 to promote formation of the complex X and/or to cause aggregation or flocculation of multiple complexes into large clusters.

Figure 3:
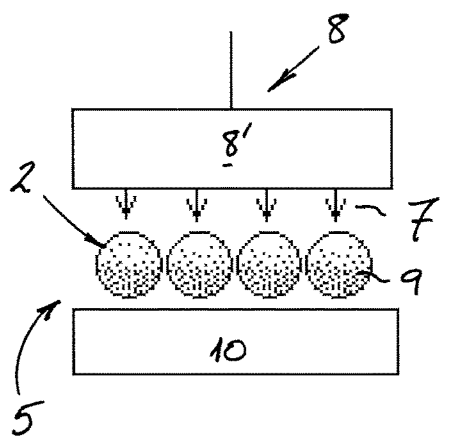
FIG. 3 is a schematic view of a treatment zone in a haemodialysis system according to another preferred embodiment.
Figure 4:
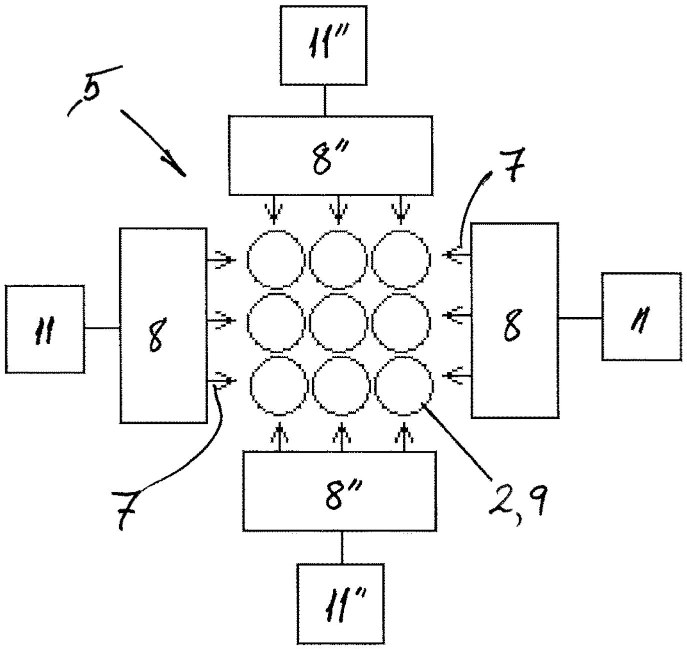
FIG. 4 is a schematic view of a treatment zone in a haemodialysis system according to a further preferred embodiment.

To this end, with reference to drawing FIGS. 3 and 4, EMR 7 may be applied by an applicator device 8 to treat the blood. Indeed, the EMR 7 may result, either directly or indirectly, in preferential inactivation or neutralisation of pathogens in the blood. The at least one applicator device 8 applies the EMR 7 via an applicator head 8' to the blood flowing through the treatment zone 5 along the extracorporeal blood flow pathway 2. The EMR 7 (e.g. DC electric current, AC magnetic field, terahertz radiation, visible light, UV radiation, X-ray and/or gamma radiation) is applied to the blood via the or each applicator head 8' to promote formation of the supramolecular complex X or aggregation or flocculation of multiple complexes X into large clusters, and to inactivate or neutralise microorganisms, pathogens, and/or molecular structures as the blood flows through the treatment zone 5.

Figure 2:
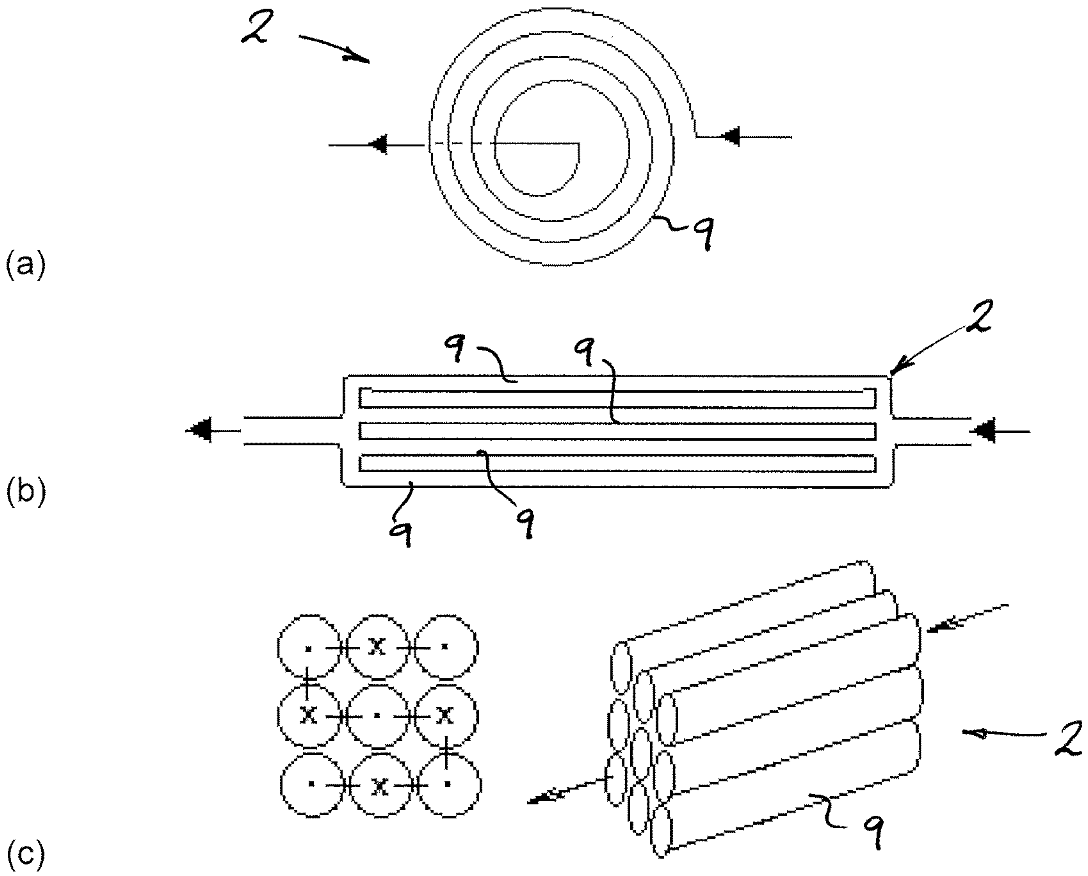
FIG. 2 shows schematic views of three variants (a) to (c) for conveying blood through a treatment zone in a haemodialysis system according to preferred embodiments.

Referring now to drawing FIGS. 2(*a*) to (*c*), three variations of the tubing 9 for the blood flow pathway 2 in the treatment zone 5 of the system 1 are shown schematically. FIG. 2(*a*) illustrates the convoluted and generally flat spiral pathway 2 for the blood in the treatment zone 5 also shown in FIG. 1. FIG. 2(*b*) illustrates an array of interconnected parallel tubes 9 that are arranged to extend side-by side through the treatment zone 5. FIG. 2(*c*), on the other hand, illustrates a stacked 3×3 array of tubing 9. In this particular case, however, the tubing 9 represents a single flexible tube that is bent in a serpentine configuration—the cross-sectional end view in FIG. 2(*c*) showing the lengths of tubing 9 in which the flow is directed "out of the page" by a central point, and the lengths in which the flow is directed "into the page" by a central cross. Those lengths are then joined by 180-degree bends in the tubing at adjacent ends of the lengths of the tubing 9 joined by a dash. In this way, referring to the perspective view in FIG. 2(*c*), the blood enters the 3×3 stacked array via the upper, right-hand-side length of tubing 9 (as shown by arrow) and leaves the 3×3 stacked array via the lower, left-hand-side length of tubing 9 (as shown by the arrow).

With reference to drawing FIG. 3, an example of treatment zone 5 in a system 1 according to a preferred embodiment is illustrated. In this example, treatment zone 5 includes a blood flow path 2 formed by four interconnected parallel tubes 9 that extend side-by side, as in FIG. 2(*b*). A magnet 10, e.g. a DC electromagnet, arranged to apply an essentially constant magnetic field over an area below the treatment zone 5. This attracts red blood cells towards that area by virtue of their iron ($Fe^{++}$) ions and thereby creates a profile of blood components with the pathogens most superficially or uppermost in the tubing 9, as illustrated by the accumulation of darker (haemoglobin) cells in a lower part of that tubing 9. The EMR 7 applied from above thus treats this superficial layer with greatest activity, thereby partially sparing deeper layers containing healthy components. Thus, a roughly vertical (non-homogenous) gradient is generated through the blood, with microorganisms, pathogens and the target molecule M located superficially and mainly red blood cells (RBCs) in a lowermost layer towards the magnet. If therapeutic EMR 7 is applied to encounter the superficial layer (with higher concentrations of pathogens), the selectivity of the treatments is enhanced, especially with shorter wavelength and higher frequency EMRs 7.

Referring now to drawing FIG. 4, a further embodiment of a treatment zone 5 in a system 1 for treating hematologic pathologies is illustrated. In this particular example, the treatment zone 5 incorporates an extracorporeal blood flow pathway 2 having a 3×3 stacked array of tubing 9 corresponding to the example shown in FIG. 2(*c*). The laterally arranged applicator devices 8, each connected to a control unit and power source 11, include an electromagnetic coil (e.g. an orthogonal pancake coil of wound copper wire) for generating and applying an AC oscillating magnetic field (OMF) 7 via applicator heads 8' arranged adjacent sides of the 3×3 stacked array of tubing 9. In addition, the treatment zone 5 includes further upper and lower applicator devices 8", each having a control unit and power source 11", for applying supplemental EMR 7' (typically of a type different to OMF) to the blood in the treatment zone 5. By applying AC electric current of certain frequencies through the two OMF coils with correct alternating sequencing, an OMF is produced that passes through the treatment zone 5. The field may be pulsed multiple times over the treatment period and combined with the other EMR 7' applied orthogonally simultaneously in combinations determined to inactivate or kill a pathogen most effectively.

Figure 6:
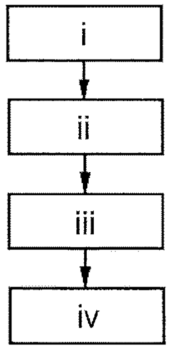
FIG. 6 is a flow diagram schematically representing a haemodialysis method according to an embodiment.

With reference to FIG. 6 of the drawings, a flow diagram is shown to illustrate schematically the steps in a method of haemodialysis for removing a target substance from the blood of a patient pursuant to the disclosure using a system 1 described above with reference to the embodiments in FIGS. 1 to 4. In this example, the disclosure is employed in a haemodialysis circuit. In this regard, the first box i of FIG. 6 represents the step of connecting an infected patient to an extracorporeal blood flow pathway 2, e.g. in a haemodialysis circuit 3, for conveying a flow of blood from the patient along the pathway 2. To this end, the vascular access is obtained in the patient in the usual way to facilitate haemodialysis in an intensive care unit (ICU). The patient will likely need to be anticoagulated. The blood is conveyed from the patient along the extracorporeal blood flow pathway 2 but does not go directly to the haemodialysis unit 4. Rather, it rather proceeds along the pathway through a treatment zone 5, which is arranged in such a way that it results in a transit time in the range of about 1 minute to 5 minutes for a blood volume in the range of about 100 mL to 300 mL of whole blood. The second box ii represents a step of infusing or administering a complexing agent, such as a supra-molecular compound C or core particle, into the blood in the extracorporeal blood flow pathway 2 adapted for binding with a target molecule M.

The third box iii of FIG. 6 represents the step of conveying the blood with the complexing agent (i.e., supra-molecular compound C) through a treatment zone 5 of the extracorporeal blood flow pathway 2 for a predetermined period of time, typically 5 to 15 mins, for binding or incorporating the target molecule M in a supra-molecular complex X and optionally applying electro-magnetic radiation (EMR) 7 to the blood passing through the treatment zone 5 during the transit time. The blood may thus be exposed to one or more type of EMR 7 selected from the group of: DC electric current, AC oscillating magnetic field (OMF), visible light, UV radiation, X-ray radiation, gamma radiation, and terahertz radiation. The EMR 7 may be applied by one or more applicator device 8 via a respective applicator head 8' arranged adjacent the tubing 9 defining the blood flow pathway 2 in the treatment zone 5. An adjuvant may be added to the blood prior to the blood entering the treatment zone 5, so that a desired photochemical, electrochemical, or magneto-chemical treatments may occur in the treatment zone 5. Upon exiting the treatment zone, any such adjuvant process will then cease.

The final box iv in FIG. 6 of the drawings represents the step of passing the blood through a dialysis/filtration unit 4 and removing the supra-molecular complex X from the blood via haemodialysis, preferably via one or more of filtration, ultrafiltration, convection, or membrane adsorption. Thus, break-down products or complexes formed during the treatment with EMR 7 are filtered out of the blood. After filtration, the treated blood completes its traverse of the extracorporeal blood flow pathway or circuit and returns into the patient. The step of passing the blood through the haemodialysis unit 4 may comprise separating or dividing the blood flow along the extracorporeal blood flow pathway 2 into two streams, with a first stream comprising substantially small molecules typically having a size less than 1.5 nm, including water and electrolytes, and a second stream comprising larger molecules typically having a size of over 3 nm and up to many microns, including larger proteins, supra-molecular structures X and blood cells. In this way, the two steams are then be processed/filtered separately in the dialysis unit. The first stream will desirably include albumen, which at a size of about 2.5 nm qualifies as a mid-sized molecule. But it is preferable not to remove albumen from the plasma due to its importance in maintaining plasma oncotic pressure. The first stream and the second stream are the re-combined into a unified extracorporeal blood flow 2 prior to returning the blood to the patient.

Approximately 20-30 such treatments may be necessary to treat an entire adult blood volume, and a further series of 20-30 such treatments may be needed as returned blood of earlier treatments mixes with blood in the patient that has not yet been treated.

Although specific embodiments of the disclosure are illustrated and described herein, it will be appreciated by persons of ordinary skill in the art that a variety of alternative and/or equivalent implementations exist. It should be appreciated that each exemplary embodiment is an example only and is not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

It will also be appreciated that the terms "comprise", "comprising", "include", "including", "contain", "containing", "have", "having", and any variations thereof, used in this document are intended to be understood in an inclusive (i.e. non-exclusive) sense, such that the process, method, device, apparatus, or system described herein is not limited to those features, integers, parts, elements, or steps recited but may include other features, integers, parts, elements, or steps not expressly listed and/or inherent to such process, method, process, method, device, apparatus, or system. Furthermore, the terms "a" and "an" used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects. In addition, reference to positional terms, such as "lower" and "upper", used in the above description are to be taken in context of the embodiments depicted in the figures, and are not to be taken as limiting this disclosure to the literal interpretation of the term but rather as would be understood by the skilled addressee in the appropriate context.

The invention claimed is:

1. A method of removing a target molecule from blood of a patient, the target molecule being a mid-sized molecule having a mass in the range of about 500 Da to 50 kDa, the method comprising steps of:

providing a complexing agent, namely a supra-molecular compound, adapted for binding or incorporating the target molecule in the blood of the patient in a complex, namely a supra-molecular complex;

administering the complexing agent into the patient's blood for binding with the target molecule;

conveying the blood having the complexing agent through a treatment zone of an extracorporeal blood flow pathway for a predetermined period of time to bind or incorporate the target molecule within the blood in the supra-molecular complex; and removing the supra-molecular complex from the blood by haemodialysis, which includes one or more of filtration, ultrafiltration, convection, or adsorption.

2. A method according to claim 1, wherein the complexing agent comprises a supra-molecular compound having an encapsulating supra-molecular structure.

3. A method according to claim 2, wherein the encapsulating supra-molecular structure comprises an ultra large cage structure (ULCS) protein.

4. A method according to claim 1, wherein the complexing agent comprises a number of individual molecules adapted to bind to the target molecule and to each other in a form of polymerization or flocculation of a target molecule into clusters or larger aggregates.

5. A method according to claim 1, wherein the predetermined period of time in the extracorporeal blood flow pathway is in the range of 2 to 20 minutes.

6. A method according to claim 1, wherein the step of administering the complexing agent into the patient's blood comprises introducing or infusing the complexing agent into the extracorporeal blood along the extracorporeal pathway.

7. A method according to claim 1, wherein the step of administering the complexing agent into the patient's blood comprises introducing or infusing the complexing agent into the patient's bloodstream one or more hours prior to performing haemodialysis to form the complex in vivo.

8. A method according to claim 1, further comprising altering physical or chemical conditions of blood in the treatment zone to promote complexing of the target molecule with the complexing agent; including altering any one or more of the pH, temperature, and/or composition of the blood in the treatment zone, and/or agitating the blood in the treatment zone.

9. A method according to claim 8, comprising applying electromagnetic radiation (EMR) to the blood in the treatment zone to promote formation of the complex or to cause aggregation or flocculation of multiple complexes into large clusters; wherein the step of applying EMR to the blood in the treatment zone includes applying one or more of: a DC electric voltage, an alternating magnetic field, terahertz radiation, visible light, ultraviolet radiation, X-ray radiation or gamma radiation.

10. A method according to claim 1, comprising a step of introducing one or more adjuvant compound(s) into the blood before it enters the treatment zone to enable a photochemical, electrochemical, or magneto-chemical process in the treatment zone.

11. A method according to claim 1, comprising separating or dividing the blood flow along the extracorporeal blood flow pathway into two streams, wherein a first stream comprises substantially small molecules having a size less than 1.5 nm, including water and electrolytes, and a second stream comprising larger molecules having a size of over 3 nm, including larger proteins, supra-molecular structures and blood cells.

12. A method according to claim 11, comprising processing the first stream and the second stream of the extracorporeal blood flow pathway separately in a haemodialysis unit via one or more of filtration, ultrafiltration, convection, or adsorption.

13. A system according to claim 11, further comprising re-combining the first stream and the second stream into a unified extracorporeal blood flow prior to returning the blood to the patient.

14. A method according to claim 1, wherein the step of conveying the flow of blood from a patient along the extracorporeal blood flow pathway includes conveying blood through a blood flow circuit, namely a haemodialysis circuit, configured to return the blood to the patient, the treatment zone being arranged in the extracorporeal blood flow pathway upstream of a haemodialysis unit.

15. A system for removing a target molecule from blood of a patient, wherein the target molecule is a mid-sized molecule having a mass in the range of about 500 Da to 50 kDa, the system comprising:

an extracorporeal blood flow pathway configured for connection to a patient and configured for guiding or conveying a flow of blood from the patient along the pathway;

a treatment zone arranged in the extracorporeal blood flow pathway for mixing a complexing agent with the blood, the complexing agent comprising a supra-molecular compound having an encapsulating supra-molecular structure adapted to bind the target molecule in a complex, namely a supra-molecular complex, as the blood flows through the treatment zone; and a haemodialysis unit for separating the complex from the blood via one or more of filtration, ultrafiltration, convection, and membrane adsorption, with or without magnetic assistance.

16. A system according to claim 15, wherein the extracorporeal blood flow pathway is part of a haemodialysis circuit configured to return the blood to the patient.

17. A system according to claim 16, wherein the treatment zone is arranged in the extracorporeal blood flow pathway upstream of the haemodialysis unit.

18. A system according to claim 15, wherein the extracorporeal blood flow pathway for guiding or conveying the flow of blood in the treatment zone is any one or more of extensive, convoluted, serpentine and tortuous.

19. A system according to claim 15, wherein the extracorporeal blood flow pathway for guiding or conveying the flow of blood comprises one or more tube or catheter.

20. A system according to claim 15, comprising at least one applicator device in the treatment zone for applying electromagnetic radiation (EMR) to the blood flowing along the extracorporeal blood flow pathway, the applicator device being adapted to emit or generate and apply any one of: DC electric voltage, alternating magnetic field, terahertz radiation, visible light, ultraviolet light, X-ray or gamma radiation.

21. A system according to claim 15, comprising a plurality of applicator devices in the treatment zone, wherein the applicator devices are configured for applying electromagnetic radiation (EMR) to blood flowing through the treatment zone simultaneously.

22. A system according to claim 21, wherein the applicator devices are adapted to emit or generate and apply the same type of EMR; and/or the applicator devices are adapted to emit or generate and apply different types of EMR.

23. A method of removing a target molecule from blood of a patient, wherein the target molecule is a mid-sized molecule having a mass in the range of about 500 Da to 50 kDa, the method comprising steps of:

providing a supra-molecular compound as a complexing agent for binding or incorporating the target molecule in the blood of the patient in a supra-molecular complex;

administering the complexing agent into the blood in an extracorporeal blood flow pathway for binding with the target molecule;

conveying the blood having the complexing agent through a treatment zone of the extracorporeal blood flow pathway for a predetermined period of time to bind or incorporate the target molecule within the blood in the supra-molecular complex; and removing the supra-molecular complex from the blood by haemodialysis.

* * * * *